United States Patent [19]

Nakahara et al.

[11] Patent Number: 4,495,294

[45] Date of Patent: Jan. 22, 1985

[54] METHOD FOR DETERMINING BACTERIAL ENDOTOXIN AND KIT THEREFOR

[75] Inventors: Chizuko Nakahara, Hino; Shigenori Tanaka, Tokyo; Hiroshi Tamura, Higashiyamato; Akiyoshi Matsumoto, Hino, all of Japan

[73] Assignee: Seikagaku Kogyo Co., Ltd., Tokyo, Japan

[21] Appl. No.: 441,810

[22] Filed: Nov. 15, 1982

[30] Foreign Application Priority Data

Nov. 16, 1981 [JP] Japan .............................. 56-182190

[51] Int. Cl.$^3$ ...................... G01N 33/16; C12Q 1/00; C12Q 1/38; C12Q 1/36
[52] U.S. Cl. ...................................... 436/502; 435/4; 435/810; 435/23; 435/24; 436/175
[58] Field of Search ................ 435/4, 7, 13, 18, 19, 435/23, 24, 29, 34, 38, 39, 184, 810; 436/175, 502, 825

[56] References Cited

U.S. PATENT DOCUMENTS

| | | | |
|---|---|---|---|
| 4,038,147 | 7/1977 | Reno | 435/13 |
| 4,067,776 | 1/1978 | Khan | 435/34 |
| 4,188,264 | 2/1980 | Iwanaga et al. | 436/502 |
| 4,370,413 | 1/1983 | Neeman et al. | 435/39 |

FOREIGN PATENT DOCUMENTS 6035994  4/1981  Japan .................................. 435/4

OTHER PUBLICATIONS

Reinhold, R. B. et al., *Proc. Soc. Exp. Biol. and Med.* vol. 137; 334-340, 1971.

Tamura, H. et al., "Perchloric Acid Treatment of Human Blood for Quantatative Endotoxin Assay Using Synthetic Chromogenic Substrate for Horseshoe Crab Clotting Enzyme" Chem. Abst. 97, 157505u, 1982.

*Primary Examiner*—Lionel M. Shapiro
*Assistant Examiner*—Jayme A. Huleatt
*Attorney, Agent, or Firm*—Sherman & Shalloway

[57] ABSTRACT

Bacterial endotoxin in an assay sample is determined by an amoebocyte lysate component of horseshoe crab in the presence or absence of a substrate for endotoxin determination by using an assay sample in the liquid state obtained by treating said assay sample with an endotoxin-free acid having a p$K_a^{25°C}$ value of not more than 3 at a pH of not more than 3; and a kit therefor, a receptacle containing (a) an endotoxin-free acid having a p$K_a^{25°C}$ value of not more than 3 e.g. perchloric acid, trichloroacetic acid, nitric acid, for treating the assay sample and a receptacle containing (b) an amoebocyte lysate component or horseshoe crab. The acid treatment of the assay sample results in improved accuracy, reliability and reproducibility of the bacterial endotoxin determination.

15 Claims, 1 Drawing Figure

Fig. 1

METHOD FOR DETERMINING BACTERIAL ENDOTOXIN AND KIT THEREFOR

This invention relates to a method for determining a bacterial endotoxin (to be sometimes abbreviated as "endotoxin"), and a kit suitable for use therein. Specifically, it relates to a method for determining an endotoxin in an assay sample such as a biological sample or a preparation of a biological sample (to be sometimes abbreviated as "assay sample") with markedly improved accuracy, reliability and reproducibility, and a kit suitable for use therein.

More specifically, this invention pertains to a method for determining a bacterial endotoxin in an assay sample by an amoebocyte lysate component of horseshoe crab in the presence or absence of a substrate for endotoxin determination, characterized in that the determination is effected by using an assay sample in the liquid state obtained by treating said assay sample with an acid having a $pKa^{25°C.}$ value of not more than 3 at a pH of not more than 3.

A method is known for determining an endotoxin in an assay sample by an amoebocyte lysate component of horseshoe crab in the presence or absence of a substrate for endotoxin determination.

In 1968, Levin reported a specific in vitro method for detecting an endotoxin using an amoebocyte lysate component of horseshoe crab. Since then, this method has been utilized as the Limulus test (LAL-Test) for the simple and rapid determination of endotoxins in basic and applied fields of medicine and pharmaceutical science. In the U.S.A., for example, the use of the LAL-Test has had statutory sanction, although under limited conditions, as a substitute for a pyrogen test on therapeutic instruments and biological preparations.

The advent of such a specific detecting method for endotoxins had recently prompted active etiological investigations by clinical medical researchers into serious pathological conditions such as endotoxemia and liver cirrhosis. Furthermore, many attempts have been made to determine an endotoxin in an assay sample by the LAL-Test in order to study the relationship of an endotoxin in a biological sample to a particular diseased condition.

It has been found, however, in the course of these works that a so-called inhibitory phenomenon or a pseudo-positive phenomenon sometimes occurs in which the gellation phenomenon of an amoebocyte lysate of horseshoe crab is inhibited in spite of the presence of an endotoxin, or such gellation occurs in the absence of an endotoxin.

Under the hypothesis that such a trouble is due to some causative substance, attempts have been made to remove the causative substance by pre-treating the assay sample, but no successful result has been reported. In addition, clinico-pathological results of the LAL-Test using such pre-treated assay samples often show disagreement of the determined endotoxin level of a blood sample of a patient with endotoxemia, carcinoma of the pancreatic duct, carcinoma of the bile duct, disseminated intravascular coagulation syndrome (DIC) and liver cirrhosis with his clinical condition, the results of bacteriall cultivation, or with other paramedical data. Thus, doubts have been cast on the utility of the LAL-Test for the detection of endotoxins in assay samples.

Accordingly, it is now time to re-assess the applicability of the LAL-Test using an assay sample such as a biological sample or a preparation of a biological sample to clinical diagnosis. Furthermore, a great recent advance in the biochemical analysis of the mechanism of gellation of an amoebocyte lysate of horseshoe crab by an endotoxin has led to the clarification of the role of factors which undergo the action of an endotoxin involved in the gellation phenomenon and the role of an enzyme system in the gellation phenomenon. Thus, the results of such a biochemical analysis have also aroused many doubts on the propriety of the detection of an endotoxin in an assay sample by the conventional LAL-Test.

Specifically, the aforesaid biochemical analysis has led to the discovery that the gellation mechanism of an amoebocyte lysate of horseshoe crab by an endotoxin is made up of a system of several kinds of inactive factors similar to a blood coagulating system of a mammal, and that a factor specific to the endotoxin is first activated in proportion to the amount of the endotoxin, then inactive factors (pro-enzymes) are successively converted stepwise to active factors (enzymes), the final factor (proclotting enzyme) is activated, the activated clotting enzyme acts on a coagulating protein precursor, coagulogen, as a substrate to form a coagulin monomer, and this monomer polymerizes to a gel-like protein [S. Iwanaga et al., FEBS Letter, 120, 217 (1980)].

Thus, it has been elucidated that the gellation phenomenon mentioned above occurs by a mechanism different from the hitherto accepted mechanism that the pro-clotting enzyme is activated directly by an endotoxin to become a clotting enzyme which then acts on the coagulogen to cause gellation.

It has also been found by a comparison of the coagulation system of the amoebocyte lysate of horseshoe crab with the blood coagulating system of a mammal that the coagulogen, the clotting enzyme and an enzyme activating the pro-clotting enzyme in the former have properties similar to the fibrinogen, factor Xa and thrombin, respectively, in the latter. The propriety of these newly discovered facts is confirmed by the fact that the amoebocyte lysate of horseshoe crab undergoes gellation by the aforesaid coagulating factors present in the blood of mammals or proteolytic enzymes such as trypsin.

A method is also employed which comprises adding an endotoxin preparation (for example, endotoxin *E. coli* 0111:B4 from *E. coli,* a product of Difco Company) to an assay sample, detecting the endotoxin in the assay sample by the LAL-Test, and determining the amount of the endotoxin in the sample from the degree of its detection. It has been found however that when this method is performed using a blood sample, a detection level corresponding to the amount of the endotoxin added cannot be ascertained, and the gellation is inhibited by the LAL-Test.

As stated hereinabove, many doubts have arisen with respect to the propriety of the determination of an endotoxin in a biological sample or a preparation of a biological sample by the conventional LAL-Test, and it is now necessary to re-assess the applicability of the LAL-Test using assay samples to clinical diagnosis or the significance of this test. Hence, unless factors which are involved in the clotting system of the amoebocyte lysate of horseshoe crab and are present in the assay samples are removed accurately, it would evidently be impossible, and even insignificant, to determine an endotoxin by the LAL-Test with accuracy, reliability and reproducibility.

The present inventors undertook a detailed study of known methods of pre-testing assay samples in the conventional LAL-Test, by utilizing the method for determining an endotoxin on a synthetic substrate with high sensitivity with an amoebocyte lysate of horseshoe crab, which was developed by the same Applicant as the present one (Japanese Laid-Open Patent Publication No. 15797/1979; U.S. Pat. No. 4,188,264; German Patent Publication DE No. 2740323).

This study has led to the important discovery that it is virtually impossible to determine an endotoxin with high accuracy and reliability by using blood samples which are pre-treated by conventional pre-treating methods for biological samples, such as blood samples, for example the chloroform treating method [J. Levin, et al., J. Lab. Clin. Med., 75, 903 (1970)], the acidification method [R. B. Reinhold et al., Proc. Soc. Exp. Biol. Med., 137, 334 (1971)], or the heating method [M. S. Cooperstock, Lancet (i) 1272 (1975)].

Further investigations have led to the discovery that as shown in detail experimentally in Examples to be given hereinafter, when a known amount of an endotoxin is added to a blood sample, and the endotoxin level detected with regard to an assay sample obtained by pre-treating the blood sample by the aforesaid conventional methods is examined by the aforesaid method using a synthetic substrate, an inhibitory factor acting on the clotting system of the horseshoe crab amoebocyte lysate present in the blood sample remains in the case of the chloroform treating method and the acidification method, and the true amount of the endotoxin present in the sample cannot be determined with accuracy and reliability. It has also been found that when the above heating method is used, the inhibitory enzyme in the blood sample can be completely inactivated, but the level of the endotoxin detected from this sample varies greatly, for example, between ⅓ to 3 times that obtained in a control, and the true amount of the endotoxin present cannot be determined with high reliability.

The present inventors furthered their investigations in order to develop a new pre-treating method capable of overcoming the aforesaid technical difficulties associated with the determination of endotoxins in blood samples pre-treated by conventional pre-treating methods, and thus to provide a method of determining an endotoxin, present in an assay sample such as a biological sample or a preparation of a biological sample with accuracy, reliability and reproducibility using an amoebocyte lysate component of horseshoe crab.

Consequently, they have found that the true amount of an endotoxin present in an assay sample can be determined by using an amoebocyte lysate component of horseshoe crab with excellent accuracy, reliability and reproducibility by a method for determining a bacterial endotoxin in the assay sample by an amoebocyte lysate component of horseshoe crab in the presence or absence of a synthetic substrate for endotoxin determination, characterized in that the determination is effected by using an assay sample in the liquid state obtained by treating said assay sample with an acid having a $pKa^{25°\ C.}$ value of not more than 3 at a pH of not more than 3.

As shown in Examples 4 and 5 given hereinafter, this method can be evaluated highly in actual clinical applications.

Thus, according to the investigations of the present inventors, the many troubles which cast doubts on the utility of the conventional LAL-Test in clinical diagnosis can be completely removed, and an endotoxin present in a biological sample can be determined by using an amoebocyte lysate of horseshoe crab by a coagulation method (gellation method) or synthetic substrate method known per se. As a result, the present invention contributes greatly to basic and applied fields of medicine and pharmaceutical science including clinical diagnosis.

It is an object of this invention therefore to provide a markedly improved method for determining a bacterial endotoxin.

Another object of this invention is to provide a kit suitable for bacterial endotoxin determination.

The above and other objects of this invention and its advantages will become more apparent from the following description.

The method itself of determining a bacterial endotoxin in an assay sample using an amoebocyte lysate component of horseshoe crab in the presence or absence of a substrate for endotoxin determination by the coagulation or synthetic substrate technique is well known, and can be used in the present invention.

Qualitative, semi-quantitative and quantitative techniques are known as the coagulating method (gellation method), and all of these can be applied to the method of this invention to perform determination with high accuracy, excellent reliability, and good reproducibility. There can be utilized the measuring method, generally called a gellation method, described in J. Levin, F. B. Bang, Bull. Johns Hopkins Hosp. 115, pages 265–274 (1964). According to the gellation method, an assay sample is contacted with an amoebocyte lysate component of horseshoe crab in the absence of a substrate for endotoxin determination, the presence of the resulting gel is observed by the naked eye, and the presence of an endotoxin is determined by the presence of the gel. In addition to the qualitative technique, there can also be used a semi-quantitative technique by performing the test using a plurality of samples diluted to varying ratios of dilution.

A quantitative technique in accordance with the gellation method described in U.S. Pat. No. 4,104,030, called the clotted protein method, can also be used. In this method, the assay sample is contacted with the amoebocyte lysate component of horseshoe crab in the absence of a synthetic substrate for endotoxin determination, and the resulting gel is collected and digested with a strong alkali. The amount of an endotoxin is measured and calculated by the photometric determination of the resulting solution.

A quantitative technique in accordance with the gelling method described in U.S. Pat. No. 4,038,029, called the turbidity test, can also be utilized. According to this method, the assay sample and the amoebocyte lysate component of horseshoe crab are contacted in the absence of a synthetic substrate for endotoxin determination, the increase in turbidity owing to the formation of a gel is measured, and the amount of an endotoxin is calculated.

As regards the aforesaid synthetic substrate method (using a synthetic substrate for endotoxin determination), some techniques using an optical method are known, and can be utilized in the present invention. For example, the method described in the above-cited U.S. Pat. No. 4,188,264 can be used. According to this method, the assay sample is contacted with the amoebocyte lysate component of horseshoe crab in the presence of a synthetic substrate for endotoxin determination, for example in the presence of a peptide-type substrate of the formula $R_1$-Gly-Arg-$R_2$ wherein $R_1$ represents a member selected from the group consisting of an L-amino acid moiety whose N-terminal is protected by a protective group, a peptide moiety consisting of an L-amino acid and protected by a protective group at its N-terminal, a D-amino acid substituted L-amino acid moiety, and a D-amino acid substituted peptide moiety consisting of an L-amino acid, and is bonded to the amino group of the glycine moiety expressed by Gly through a peptide bond; and $R_2$ represents a chromogenic moiety which is bonded to the C-terminal of an L-arginine moiety expressed by Arg through an acid amide bond and/or ester bond and can be enzymatically hydrolyzed in the presence of the amoebocyte lysate component of horseshoe crab.

The $R_2H$ which is liberated is measured by an optical technique, and the amount of an endotoxin can be calculated. The measurement according to the aforesaid optical technique can be made by using light of suitable wavelengths which differ according to the kind of the substrate used and correspond to the kind of $R_2H$ to be liberated. For example, when PNA (p-nitroaniline) is liberated, light having a wavelength of 405 nm can be used. When AMC (7-amino-4-methylcoumarine) is liberated, the measurement can be done by using light having an exciting wavelength of 380 nm and a measuring wavelength of 460 nm. When DEAA (diethylaminoaniline) is liberated, there are absorptions at 510 nm and 550 nm, and in this case, it is preferred to perform the measurement after converting it to a dye which is more suited for observation, as will be described hereinafter.

It is now possible to employ a technique of performing the measurement after the liberated $R_2H$ is converted to another colored compound. For example, in the case of PNA, it may be coupled with a coupling reagent to form an azo dye having a color more suitable for observation in accordance with the technique discribed in R. B. Friedman, H. C. Kwann, and M. Szczeinski, Thromb. Res. 12, pages 37–46 (1977), and then the measurement may be done by using light having a wavelength of 545 nm. DEAA may also be coupled with a coupling reagent to form a colored dye easier for observation, and the measurement may be made by using light having a wavelength of 660 nm.

A method for preparing the amoebocyte lysate component of horseshoe crab used in the aforesaid known gellation method or synthetic substrate method is known, and it is commercially available. For example, it can be prepared by the methods described in J. Biochem. 80, pages 1011–1021 (1976); Japanese Patent Publication No. 40131/1976; U.S. patent application Ser. No. 489,224, now U.S. Pat. No. 4,096,091; corresponding to Japanese Laid-Open Patent Application No. 27994/76; U.S. Pat. No. 4,107,077; U.S. Pat. No. 4,301,245; FEBS Letter, 120, pages 217–220 (1980); FEBS Letter, 129, pages 318–321 (1981); and BBRC, 105 (2), pages 717–723 (1982). Examples of commercially available products of the lysate component include the following trademarked products Pregel (Seikagaku Kogyo Co., Ltd., Japan), E. Toxate (Sigma Co., Ltd., U.S.A.), Pyrotest (Difco Lab., U.S.A.). Limulus Test Wako (Cape Cod Assoc., U.S.A.), Pyrogent (Mallincrodt Chem. Works, U.S.A.), Pyrosperse (Mallincrodt, Chem. Works, U.S.A.), Pyrosate (Haemachem, U.S.A.), Frozen LAL (Microbiological Associates, U.S.A.), Finished LAL (Microbiological Associates, U.S.A.), Pyrostat (Worthington Biochemical Corp., U.S.A.), and LAL (Ocean Tech., U.S.A.).

The following substrates are known and easily available for determination of endotoxins using the synthetic substrate method. In the following exemplification, the symbols have the following meanings.

Bz: benzoyl; Ile: isoleucine; Glu: glutamic acid; $\gamma$-OME: the methyl ester of the carboxyl group at the $\gamma$-position; Gly: glycine; Arg: arginine; PNA: p-nitroanilide; Tos: p-toluenesulfonyl; Boc: tert-butoxycarbonyl; Val: valine; Leu: leucine; Ser: serine; 5-NNA: 5-nitro-$\alpha$-naphtylamide; $\beta$-NA: $\beta$-naphthylamide; INDE: indoxyl ester; Z: carbobenzoxy; MINDE: N-methylindoxyl ester; O.Bz: O-benzoyl; MCA: 4-methylcoumarine amide; DEAA: p-diethylaminoanilide; N.Ac: N-acetyl.

No. 1: Bz-Ile-Glu(-$\gamma$-OMe)-Gly-Arg-PNA
No. 2: Tos-Ile-Glu-Gly-Arg-PNA
No. 3: N.Ac-Ile-Glu-Gly-Arg-PNA
No. 4: Boc-Val-Leu-Gly-Arg-PNA
No. 5: Bz-Val-Gly-Arg-PNA
No. 6: Boc-Val-Ser-Gly-Arg-PNA
No. 7: Boc-Val-Gly-Arg-PNA
No. 8: Boc-Leu-Gly-Arg-PNA
No. 9: Boc-Ser-(-O.Bz)-Gly-Arg-PNA
No. 10: Bz-Val-Ser-Gly-Arg-5-NNA
No. 11: D-Val-L-Leu-Gly-Arg-5.NNA
No. 12: Bz-Val-Leu-Gly-Arg-$\beta$-NA
No. 13: Tos-Ile-Glu-Gly-Arg-$\beta$-NE
No. 14: Boc-Val-Gly-Arg-INDE
No. 15: Z-Val-Leu-Gly-Arg-4-methyl umbelliferyl ester
No. 16: Bs-Val-Ser-Gly-Arg-Resorufin ester
No. 17: D-Val-L-Ser-Gly-Val-Ser-Gly-Arg-MINDE
No. 18: D-Val-L-Leu-Gly-Arg-$\alpha$·NA
No. 19: D-Val-L-Leu-Gly-Arg-Resorufin ester
No. 20: Boc-Val-Leu-Gly-Arg-MCA
No. 21: Boc-Leu-Gly-Arg-MCA
No. 22: Z-Leu-Gly-Arg-MCA
No. 23: Boc-Ile-Glu-Gly-Arg-MCA
No. 24: Boc-Val-Ser-Gly-Arg-MCA
No. 25: Boc-Ser(-O·Bz)-Gly-Arg-MCA
No. 26: Boc-Ser-Gly-Arg-MCA
No. 27: Boc-Leu-Gly-Arg-DEAA
No. 28: Bz-Leu-Gly-Arg-DEAA
No. 29: Boc-Val-Leu-Gly-Arg-DEAA
No. 30: Bz-Val-Deu-Gly-Arg-DEAA
No. 31: Boc-Ser-Gly-Arg-DEAA
No. 32: Bz-Ser-Gly-Arg-DEAA
No. 33: Boc-Val-Ser-Gly-Arg-DEAA
No. 34: Bz-Val-Ser-Gly-Arg-DEAA Nos. 1 to 9 are yellow and can be converted to red by coupling.

Nos. 10 and 11 are orange.

Nos. 12 to 26 are fluorescent.

Nos. 27 to 34 are used for determination after being converted to blue by coupling reangents.

According to one emodiment of determination using the know synthetic substrate method, $R_2H$ can be liberated by adding an assay sample treated with an acid having a $pKa^{25°\ C.}$ value of not more than 3 to the above-exemplified amoebocyte lysate of horsehose crab, preincubating the mixture at 37° C. for 15 to 60 minutes, then adding the above-exemplified substrate for endotoxin determination, and reacting the mixture at 37° C. for 5 minutes at a pH of about 7 to 9. According to another embodiment, R₂H can be liberated by mixing the lysate component with the substrate solution, adding the assay sample, and reacting the mixture for 30 minutes under the aforesaid pH and temperature conditions. Alternatively, the lysate component, the substrate solution and the assay sample may be mixed simultaneously and reacted to liberate R₂H. Such a measuring technique can be performed in various embodiments which are described in detail in the following publications, for example, and can be utilized in the practice of the method of this invention. Haemostatis, 7, pp. 183–188 (1978); J. Biochem., 81, pp. 1567–1569 (1977); and Endoxitoxins and Their Detection with the Limulus Ambecoyte Lysate Test, pp. 173–182 (1982 Alan R. Liss, Inc., 150 Fifthh Avenue, New York, N.Y. 10011, U.S.A.).

The method of this invention is characterized, in the determination of a bacterial endotoxin in an assay sample by an amoebocyte lysate component of horseshoe crab in a customary manner in the presence or absence of a substrate for endotoxin determination, by the fact that the determination is effected by using an assay sample in the liquid state obtained by treating said assay sample with an acid having a $pKa^{25°\ C.}$ value of not more than 3 at a pH of not more than 3. This acid treatment gives an assay sample free from the hydrolytic activity of an endotoxin-independent enzyme, which is an inhibiting factor in measuring the true amount of the bacterial endotoxin in the assay sample.

In the above-mentioned known acidification method, glacial acetic acid having a $pKa^{25°\ C.}$ value of 4.76 is used, and this method cannot give an assay sample in which the hydrolytic activity of an endotoxinindependent enzyme is no longer detected. According to the known acidification method, 1 ml of a plasma sample is treated with 0.1 ml of 25% glacial acetic acid (2.9N, pH 2.2) at a pH of 4.0, and subsequently the treated sample is neutralized. As will be shown experimentally in Table 1 hereinafter, the aforesaid hydrolytic activity is detected in the treated sample, and this shows that ther exists a factor which affects the determination of the true amount of an endotoxin in the sample. It is impossible therefore to measure the true amount of the endotoxin by using an assay sample treated by this acidification method.

According to the method of this invention, an assay sample such as a biological sample or a preparation of a biological sample is pre-treated with an acid having a $pKa^{25°\ C.}$ value of not more than 3 at a pH of not more than 3.

Illustrative of acids which can be used in this acid treatment are mineral acids such as nitric acid (−1.4), phosphoric acid (2.1), hydrochloric acid (less than 1), and sulfuric acid (less than 1); halogenic acids such as chloric acid (−1.0) and bromic acid (less than 1); perhalogenic acids such as perchloric acid (less than 1); and haloacetic acids such as monochloroacetic acid (2.9), dichloroacetic acid (1.3), trichloroacetic acid (0.7), monofluoroacetic acid (2.7), difluoroacetic acid (1.2), trifluoroacetic acid (0.23) and monobromoacetic acid (2.9). The parathensized figures show $pKa^{25°\ C.}$ values.

By pre-treating the assay sample with an acid having a $pka^{25°\ C.}$ value of not more than 3 at a pH of not more than 3, an oxidizing or denaturing action can be exerted on proteins or cell granules in the sample which have factors adversely affecting the measurement of an endotoxin by the horseshoe crab amoebocyte lysate component, whereby these factors are inactivated and removed out of the measuring system. By using the acid-treated assay sample in the liquid state, a bacterial endotoxin in the sample can be determined with markedly endotoxin in the sample can be determined with markedly improved accuracy, reliability and reproducibility by the aforesaid known coagulation method (gelling method) or synthetic substrate method.

Optimal conditions for the acid treatment, such as the concentration of the acid, and the treating temperature and time, may be selected properly depending upon the kind of the acid having a $pKa^{25°\ C.}$ value of not more than 3. Such treating conditions can be easily prescribed experimentally.

A preliminary experiment for this purpose can be conducted, for example, as follows:

A portion of the assay sample before acid-treatment is taken, and its amidase activity is measured by using a synthetic substrate, Boc-Leu-Gly-Arg-PNA, whereby the hydrolytic acitivty of an endotoxin-independent enzyme in the sample is measured. Separately, another portion of the untreated sample is treated with an acid to be used in the acid treatment, at a pH of not more than 3 at varying temperatures for varying periods of time. The resulting precipitate is centrifugally removed, and the supernatant liquid is neutralized with a base. The amidase activity of the neutralized sample is measured by using the aforesaid synthetic substrate. The acid concentration and the treating temperature and time, under which conditions the premeasured hydrolytic activity in the acid-treated sample is no longer detected, are selected. These selected conditions may be used after confirming that the endotoxin in the assay sample is not greatly inactivated under these conditions. This confirmation can be made, for example, as shown in Table 4 given hereinafter.

According to the method of this invention, the assay sample is treated with the above-exemplified acid having a $pKa^{25°\ C.}$ value of not more than 3 under suitable conditions which can be prescribed as described above. The denatured inactivated precipitate that separates in the treating system is removed from the treating system by such a means as filtration on a filter paper or centrifugal separation, and then, the residue is neutralized. By using the so prepared sample, a bacterial endotoxin in the sample is determined by an amoebocyte lysate component of horseshoe crab using the aforesaid known techniques.

The pH of the system can be adjusted properly depending upon the technique of measurement. For example, when the gellation technique is used, the pH is preferably adjusted to about 6 to about 7. When the synthetic substrate technique is used, the pH is adjusted preferably to about 7 to about 9. Examples of alkalies for the pH adjustment (neutralization) include inorganic alkalies such as the hydroxides or carbonates of alkali metals or alkaline earth metals and ammonium hydroxide, and organic bases such as basic amines, amino compounds and fatty acid salts or alkali metals. Specifically illustrative of the inorganic alkalies are sodium hydroxide, potassium hydroxide, lithium hydroxide, calcium hydroxide, magnesium hydroxide, ammonium hydroxide, sodium carbonate, potassium carbonate, calcium carbonate, magnesium carbonate and strontium carbonate. Specifically illustrative of the organic bases are mono-, di- and tri-ethanolamines, trimethylamine, triethylamine, tris-hydroxymethylaminomethane and sodium oxalate.

A wide range of non-treated samples, such as biological fluids or preparations thereof (or biologicals) are used as the assay sample to be treated with an acid having a pKa$^{25°\,C.}$ value of not more than 3.

The biological fluids are those containing proteins or cell granules susceptible to endotoxin adsorption, for example plasma, serum, blood, fractions (e.g., albumin and globulins), and circulating fluids or excretions in and out of the body, such as ascites, articular fluid and urine.

These biologicals may also include, for example, bacterial vaccines such as cholera, typhoid fever and whooping cough vaccines; viral vaccines such as influenza and Japanese B encephalitis vaccines; and blood preparations such as human immunoglobulin, pepsin-treated human immunoserum globulin, histamine-added human immunoglobulin, fibrin film, human serum albumin preparation, dried human plasma and heated human plasma protein.

In contrast to the use of an assay sample treated by the conventional methods, the use of an assay sample treated with an acid having a pKa$^{25°\,C.}$ value of not more than 3 at a pH of not more than 3 makes it possible to determine the true amount of a bacterial endotoxin in the assay sample with markedly improved accuracy, reliability and reproducibility by using an amoebocyte lysate component of horseshoe crab without the effects of inhibitory substances or pseudopositive inducing substances in the sample and also the effects of the type of diseases and the kind of the assay sample.

The method of this invention can be utilized for endotoxin determination of assay samples taken from a wide range of patients with diseases induced by infection of Gram-negative bacteria such as endotocemia including fungemia, endotoxemia, peritonitis, cephalomeningitis, urinary tract infection, and post-operative infection; liver diseases such as hepatitis and liver cirrhosis, in which a failure of the reticuloendothelial system is anticipated as a cause; anticipation of the causative relation between acute suppurative cholangitis, cholecystitis, choledocholithiasis, etc. occurring in the bile dict and a group of bacteria in the intestines; ileus; ulcerative colitis; pancreatitis; DIC (disseminated intravascular coagulaton syndrome); and a failure of the function of the reticuloendothelial system in the last stage, such as cancer, diabetes, and nephritis.

According to another aspect of this invention, there can be provided a kit for determination of a bacterial endotoxin in an assay sample, consisting essentially of a combination of (a) an endotoxin-free acid having a pKa$^{25°\,C.}$ value of not more than 3, which is essential in the method of this invention described above, and (b) an amoebocyte lysate component of horseshoe crab. Specifically, this invention provides a kit for determination of a bacterial endotoxin in an assay sample by an amoebocyte lysate component of horseshoe crab in the presence or absence of a substrate for endotoxin determination, said kit consisting essentially of a combination of a receptacle containing an acid having a pKa$^{25°\,C.}$ value of not more than 3 for the treatment of the assay sample and a receptacle containing the amoebocyte lysate component of horseshoe crab.

The kit of this invention may further contain an endotoxin-free substrate (c) for bacterial endotoxin determination required for measurement by the aforesaid synthetic substrate method. The substrate may be included in the receptacle containing the lysate component of horseshoe crab, or may be included in a separate receptacle.

The kit of this invention may further include a receptacle containing an endotoxin-free alkali (d) as exemplified hereinabove for neutralization of the acid-treated assay sample. The kit of this invention may further include a receptacle containing an endotoxin-free diluent or its frozen product (e) which is used to dilute the assay sample when it has a high concentration, or to dissolve any dry component present in the unit components to be combined into the kit, such as the lysate component (b), the substrate (c), the alkali (d), an endotoxin-free buffer (f) to be described hereinafter, the coupling reagent (g) described hereinabove, and a controlling endotoxin (h) to be described hereinafter.

The kit of this invention may further include a receptacle containing the endotoxin-free buffer (f). The buffer (f) may be in any desired form such as a dry product, a liquid, or its frozen product.

The buffer (f) and the endotoxin-free diluent or its frozen product (e) may be a common material, in which case the two materials in amounts required for the respective purposes may be included in one receptacle or in separate receptacles.

Examples of such a diluent or its frozen product (e) are endotoxin-free water, physiological saline, various buffers in the dry state, solutions thereof, and frozen products of the solutions. Specific examples of the substance (e) are tris-HCl, Good's buffers (such as HEPES, TES, TAPS, MOPS, EPPS, tricine, bicine, PIPES, and MES), triethanolamine-HCl, diethanediamine-HCl, imidazole-HCl, phosphates, boric acid-borax, borate-KCl-NaOH, borax-HCl, glycine-NaOH, 2-amino-2-methyl-1,3-propanediol-HCl, citrate, citratephosphate, maleate, tris-maleate, Veronal, and Cacodylate.

The substance (e) exemplified above may contain a non-ionic surface-active agent such as commerically available Tween 20, Tween 40, Tween 60, Tween 80, Tween 85, and Triton X-100 (tradenames).

The buffer (f) may be the same substances as (e) exemplified above which are in the form of a dry solid, its solution or a frozen product of the solution.

The kit of this invention may further contain a receptacle containing the coupling reagent (g), and/or a receptacle containing an endotoxin (h) for controlling purposes.

The coupling reagent (g) may be a known coupling agent, for example a combination of sodium nitrite, ammonium sulfamate, N-(1-naphthyl)ethylenediamine dihydrochloride and hydrochloric acid; a combination of sodium nitrite and dimethylphenol; and a combination of periodic acid, boric acid and 1-naphthol-2-sulfonic acid.

The controlling endotoxin (h) may be used in calculating the amount of an endotoxin in the assay sample from the result of the assay.

As stated above, the kit of this invention consists essentially of a receptacle containing (a) the acid having a pKa$^{25°\,C.}$ value of not more than 3 and a receptacle containing (b) the amoebocyte lysate component of horseshoe crab, and optionally comprises at least one receptacle containing at least one material selected from the group consisting of (c), (d), (e), (f), (g) and (h) described hereinabove.

Examples of such a combination are (a)-(b)-(c), (a)-(b)-(c)-(d), (a)-(b)-(c)-(d)-(e), (a)-(b)-(c)-(d)-(e)-(f), (a)-

(b)-(c)-(d)-(e)-(f)-(g), (a)-(b)-(c)-(d)-(e)-(f)-(g)-(h), (a)-(b)-(d), (a)-(b)-(e), and (a)-(b)-(f).

If further desired, it is possible to combine the kit of this invention with instruments for mixing the components, for example an endotoxin-free test tube or an endotoxin-free pipette.

The following Examples and Comparative Examples illustrate the method of this invention in greater detail.

(1) Sampling and preparation of a biological assay sample

Body fluids (e.g., plasma, serum, ascites, articular fluid, cerebrospinal fluid, or urine) of normal healthy persons or patients are collected with sufficient care taken not to permit contamination by bacteria or endotoxins.

For example, the plasma is taken from the vein of a human at his forearm elbow into a test tube containing an anticoagulating agent such as heparin, sodium citrate or disodium EDTA by using a vacuum blood drawing tube (venogect tube, a product of Terumo Co., Ltd., Japan), and separated into blood cells and plasma by centrifugation (150× g, 10 minutes). Fractions containing platelets are collected and used as a plasma sample (PRP).

A serum sample is prepared by taking the blood from the vein of a human at his elbow into a clean, endotoxin-free glass Spit test tube, allowing it to stand at room temperature for 30 minutes, centrifuging the resulting clot at 2,500 to 3,000 rpm for 10 minutes, and placing the supernatant into another endotoxin-free test tube.

The ascites, articular fluid and cerebrospinal fluid are taken by local paracentesis.

(2) Determination of a bacterial endotoxin

This was performed by the LAL-Test in accordance with the synthetic substrate technique using an endotoxin micro-determination reagent, PYRODIC (a tradename for a product of Seikagaku Kogyo Co., Ltd., Japan, prepared in accordance with Japanese Lain-Open Patent Publication No. 15797/1969 (corresponding to U.S. Pat. No. 4,188,264 and German Patent Publication DE No. 2740323)). The result was calculated for an endotoxin derived from $E.\ coli$ 0111:B4.

(3) Determination of the hydrolytic activity of an endotoxin-independent enzyme in the assay sample (to be referred to as the amidase activity)

The hydrolytic activity of an endotoxin-independent enzyme in the assay sample shows the activity of the endotoxin-independent enzyme to cleave a peptide synthetic substrate Boc-Leu-Gly-Arg-PNA (a product of Seikagaku Kogyo Co., Ltd., Japan) in the absence of the amoebocyte lysate component of horseshoe crab. It is expressed by the amount of free PNA (paranitroaniline) measured in accordance with the determination of endotoxin described in (2) above, which is calculated for an endotoxin derived from $E.\ coli$ 0.111:B4.

(4) Treatment of the biological sample (4-1) Example of this invention (treatment with perchloric acid {PCA})

To 0.1 ml of the biological sample shown in (1) above was added a 5% aqueous solution of perchloric acid so that the final concentration of the sample was 1.5%. The sample was incubated at 37° C. for 20 minutes. The resulting precipitate was centrifuged at 3,000 rpm for 15 minutes. The supernatant liquid was collected and neutralized to a pH of about 6.5 to 8.0 using a 0.2N aqueous solution of sodium hydroxide to give an acid-treated biological sample.

(4-2) Example of the invention (treatment with trichloracetic acid {TCA})

To 0.1 ml of the biological sample shown in (1) above was added the same amount of a 5% aqueous solution of trichloracetic acid, and the sample was incubated at 45° C. for 10 minutes. The resulting precipitate was centrifuged at a speed of 3,000 rpm for 15 minutes. The supernatant liquid was collected, and neutralized to a pH of 6.5 to 8.0 using a 0.1N aqueous solution of sodium hydroxide to give an acid-treated biological sample.

(4-3) Example of the invention (treatment with nitric acid {HNO})

To 0.1 ml of the biological sample shown in (1) above was added the same amount of a 3% aqueous solution of $HNO_3$, and the sample was incubated at 40° C. for 10 minutes. The resulting precipitate was centrifuged at 3,000 rpm for 15 minutes. The supernatant liquid was collected, and neutralized to a pH of about 6.5 to 8.0 using a 0.2N aqueous solution of sodium hydroxide to give an acid-treated biological sample.

(4-4) Comparative Example (treatment with chloroform)

In accordance with the description of J. Lab. Clin. Med., 75, 903 (1970), 1 part by volume of chloroform was added to 4 parts by volume of the biological sample (heparinized plasma) shown in (1) above. The mixture was vigorously shaken and stirred at 25° C. for 60 minutes, and then centrifuged at 1,100 G for 10 minutes to separate it into three layers. The intermediate layer was taken, and used as a chloroform-treated biological sample.

(4-5) Comparative Example (acidification treatment)

In accordance with the description of Proc. Soc. Exp. Biol. Med., 137, 334 (1971), 0.1 ml of 25% glacial acetic acid (2.9N, pH 2.2) was added to 0.1 ml of the biological sample shown in (1) above to decrease the pH of the system to 4.0±0.1, and subsequently, 0.2 ml of a 50% (W/V) anhydrous dibasic potassium phosphate buffer (50% $K_2HPO_4$, pH 9.4) was added to adjust the pH of the plasma to 6.3±0.1 to give an acidified biological sample. (4-6) Comparative Example (heat-treatment)

In accordance with the description of Lancet (i) 1272 (1975), the biological sample (plasma) shown in (1) above was diluted to 3 times by using a pyrogen-free sterilized distilled water, and heated at 100° C. for 10 minutes to give a heat-treated biological sample.

(4-7) Comparative Example (alkali treatment)

To 0.2 ml of the biological sample shown in (1) was added to 0.2 ml of a 0.2N aqueous solution of sodium hydroxide, and the sample was incubated at 37° C. for 10 minutes. Then, 0.2 ml of a 0.2N aqueous solution of HCl was added to neutralize it to a pH of 6.5 to 8.0 to give an alkali-treated biological sample.

EXAMPLE 1 AND COMPARATIVE EXAMPLES 1 TO 4

The amidase activity of each of the acid-treated biological samples described in (4-1) to (4-3), the comparative treated biological samples described in (4-4) to (4-7) and the non-treated biological sample shown in (1) was measured in accordance with the procedure shown in (3) above. The results are shown in Table 1.

TABLE 1

| Biological sample | Plasma | Serum | Urine | Ascites | Cerebro-spinal fluid | Articular fluid |
|---|---|---|---|---|---|---|
| Non-treated (control) | ++ | +++ | +~± | ± | − | ++ |
| PCA treated [invention (4-1)] (Example 1) | − | − | − | − | − | − |
| TCA treated [invention (4-2)] (Example 1) | − | − | − | − | − | − |
| HNO₃ treated [invention (4-3)] (Example 1) | − | − | − | − | − | − |
| Heat-treated [Comparative Example 1 (4-6)] | − | − | − | − | − | − |
| Alkali-treated [Comparative Example 2 (4-7)] | − | − | − | − | − | − |
| Chloroform-treated [Comparative Example 3 (4-4)] | +++ | +++ | +~± | ± | − | ++ |
| Acidified [Comparative Example 4 (4-5)] | + | ++ | +~± | ± | − | + |

The above symbols show the following. The amidase activity calculated for an endotoxin derived from *E. coli* 0111:B4 per ml of the biological sample:
−: 30 pg>
±: 30–70 pg
+: 70–170 pg
++: 170–700 pg
+++: 700 pg<

It is seen from the results shown in Table 1 that no remaining amidase activity was noted in the biological samples acid treated in accordance with this invention and the comparative biological samples which were heat-treated and alkali-treated, but that in the chloroform-treated and acidified biological samples in the comparative examples, the amidase activity became higher than that of the control sample (non-treated) or did not substantially disappear. This fact shows that these latter comparative samples retained the hydrolytic activity of an endotoxin-independent enzyme, and the true amount of an endotoxin in these biological samples cannot be determined accurately.

As shown in the control sample (non-treated) in Table 1, the cerebrospinal fluid normally has no amidase activity, but depending upon the time of sampling or the condition of the patient, it may have amidase activity owing to the inclusion of blood, for example.

EXAMPLE 2 AND COMPARATIVE EXAMPLES 5 AND 6

Experiments were performed using those samples of the invention and the heat-treated and alkali-treated samples of the comparison which were found to have no amidase activity from the results of Example 1 and Comparative Examples 1 to 4.

A predetermined known amount of an endotoxin was added to each of the biological samples shown in Table 2 and then the mixture was treated in the same way as in Example 1 and Comparative Examples 1 and 2. Separately, these biological samples were treated in the same way as in Example 1 and Comparative Examples 1 and 2, and then a predetermined known amount of an endotoxin was added.

The amount of the endotoxin was measured by the method described in section (2) given hereinabove using each of these samples. The percent detection, which is the percentage of the amount of the endotoxin detected and determined based on the known amount of the endotoxin added, was calculated. The results are shown in Table 2.

Table 2 shows data of the PCA-treated sample as a typical example of the acid-treated samples of the invention described in (4-1) to (4-3). Much the same results were obtained with the other samples of the invention.

In the table, (×3), (×6), and (×9) represent the ratios of dilution of assay samples at the time of measurement.

TABLE 2

(Percent detection of the added endotoxin)

| Biological sample | | Plasma | Serum | Urine | Ascites | Cerebro-spinal fluid | Articular fluid |
|---|---|---|---|---|---|---|---|
| PCA treated [invention, (4-1)] (Example 2) | Treated after addition of the endotoxin | (× 3) 95 (× 6) 105 (× 9) 104 | (× 3) 95 (× 6) 102 (× 9) 105 | 98 | (× 6) 110 | 100 | (× 6) 106 |
| | Treated before addition of the endotoxin | (× 3) 108 (× 6) 105 (× 9) 105 | (× 3) 101 (× 6) 106 (× 9) 104 | 101 | (× 6) 105 | 100 | (× 6) 115 |
| Heat-treated (Comparative Example 5) | Treated after addition of the endotoxin | (× 3) 12 (× 6) 26 (× 9) 58 | (× 3) 2 (× 6) 18 (× 9) 41 | 74 | (× 6) 45 | 100 | (× 6) 44 |
| | Treated before addition of the endotoxin | (× 3) 121 (× 6) 158 (× 9) 205 | (× 3) 21 (× 6) 44 (× 9) 68 | 82 | (× 6) 60 | 100 | (× 6) 145 |

TABLE 2-continued (Percent detection of the added endotoxin)

| Biological sample | | Plasma | Serum | Urine | Ascites | Cerebro-spinal fluid | Articular fluid |
|---|---|---|---|---|---|---|---|
| Alkali-treated (Comparative Example 6) | Treated after addition of the endotoxin | (× 3) 26<br>(× 6) 97<br>(× 9) 121 | (× 3) 13<br>(× 6) 23<br>(× 9) 37 | 78 | (× 6) 63 | 100 | (× 6) 49 |
| | Treated before addition of the endotoxin | (× 3) 29<br>(× 6) 71<br>(× 9) 105 | (× 3) 39<br>(× 6) 58<br>(× 9) 60 | 86 | (× 6) 77 | 100 | (× 6) 162 |

The results given in Table 2 demonstrate that the results of measurement using the heat-treated sample and the alkali-treated sample of the Comparative Examples which were found to have no amidase activity in the tests shown in Table 1 did not at all show a correlation to the amount of the endotoxin added, but only a part of the endotoxin added could be detected, or the percent detection was several times that of the theoretical value, and that the percent detection varied greatly depending upon the degree of dilution. It is seen therefore that the true amount of the endotoxin in these biological samples treated by the techniques shown in the Comparative Examples cannot be determined with good accuracy, reliability and reproducibility.

In contrast, when the acid-treated biological samples in accordance with this invention are used, the amount of the endotoxin can be determined at a percent detection of almost 100% with high accuracy, high reliability and good reproducibility irrespective of the ratio of dilution and the type of the biological samples, and of whether the endotoxin is added before or after the treatment.

Plasma and serum were used as biological samples and treated in the same way as in Example 2 and Comparative Examples 5 and 6, and the amount of proteins remaining in each of the samples was determined by the Lowry method {O. H. Lowry et al.: J. Biol. Chem., 193, 265 (1951)}. The results are shown in Table 3. The unit of the figures in the table is mg of protein/ml of sample. The figures were obtained as an average of three replicates. The substances named under the headline "plasma" show the anticoagulating agents used. Table 3 also contains the result of protein determination obtained with the acidified biological sample described in section (4-5) hereinabove.

TABLE 3

| Method of treatment | Plasma | | | Serum |
|---|---|---|---|---|
| | Heparin | Citric acid | EDTA | |
| Non-treated (control) | 75.0 | 77.0 | 77.0 | 68.0 |
| PCA-treated (invention) | <1 | <1 | <1 | <1 |
| Heat-treated (comparison) | 67.2 | 61.6 | 51.9 | 64.9 |
| Alkali-treated (comparison) | 75.6 | 64.5 | 75.9 | 61.6 |
| Acidified (comparison) | 72.3 | 67.3 | 67.7 | 64.3 |

The results in Table 3 show that the proteins in the non-treated sample (control) were scarcely removed in the case of the heat-treated, alkali-treated and acidified samples in the Comparative Examples, whereas the proteins were removed to a very small residual amount on the order of less than 1 mg/ml with the samples subjected to the acid-treatment in accordance with the method of this invention.

As is well known, in view of the reaction of an endotoxin-independent enzyme in a non-treated assay sample with an amoebocyte lysate component of horseshoe crab or the general protecting effect of proteins for endotoxins, it is very desirable in regard to the accuracy, reliability and reproducibility of measurement to impart a sufficient protein-removing effect to the sample without a substantial inactivating action on the endotoxin in the assay sample which is to be determined. It is seen from the results shown in Tables 2 and 3 that according to the method of this invention, this desire can be advantageously achieved.

EXAMPLE 3

The most important feature of the acid treatment in the method of this invention is that LAL-Test inhibiting factors and amidase activity present in a biological sample and such inhibiting factors as proteins or cell granules present therein which have adsorbability to an endotoxin to be determined can be decomposed or denatured and removed from the sample without exerting an undesirable deactivating action on the endotoxin.

A plasma sample to which an endotoxin derived from $E.\ coli$ 0111:B4 had been added was subjected to the PCA treatment, TCA treatment and $HNO_3$ treatment, respectively, in accordance with this invention. Separately, an endotoxin derived from $E.\ coli$ 0111:B4 was added to physiological saline, and then the mixture was subjected to each of the aforesaid acid-treatments to prepare three comparative samples.

The percent detection of the added endotoxin and the remaining amidase activity of the treated plasma samples (PRP) were determined using the resulting samples. The results are shown in Table 4. The measurements were made as follows:

To 0.1 ml of plasma from a normal healthy person was added a solution of the endotoxin in a proportion of 1000 pg per ml of the plasma. Then, each of an aqueous PCA solution, an aqueous TCA solution and an aqueous $HNO_3$ solution was added to an acid concentration of 0% (control: not added), 0.5%, 1%, 1.25%, 2.0%, 2.5%, 5% and 10%, respectively. Each of these samples was incubated at 37° C. for 10 minutes, and then centrifuged at 3,000 rpm for 15 minutes. From 50 to 100 microliters of the supernatant was collected, and neutralized to a pH of 6.5 to 8.0 using a 0.1-0.2N aqueous solution of sodium hydroxide to form test solutions. The endotoxin was determined by the method described in section (2) above using the peptide-type synthetic substrate shown in section (3) above.

As a control, the same test was conducted using physiological saline (for injection) instead of the plasma sample. The endotoxin determined on the control samples was taken as 100, and the percent detection (%) was calculated.

Furthermore, instead of the endotoxin solution, physiological saline was added to a plasma sample (PRP) of a normal healthy person, and the mixture was subjected to the PCA treatment, TCA treatment and HNO₃ treatment, respectively, as above, and the remaining amidase activities of the prepared samples were measured in the same way as above.

The results are shown in Table 4.

(a patient with endotoxemia, 38, f), a serum sample from U. H. (a patient with liver cirrhosis, 67, m), a urine sample from M. S. (a patient with urinary tract infection, 43, f), and an ascites sample from S. O. (a patient with malignant tumor of the pancreas, 54, m). To each of those biological samples which were found to contain an endotoxin was added the same amount of an endotoxin derived from *E. coli* 0111:B4 as that of the endotoxin detected. Then, the endotoxin was determined.

TABLE 4

| Acid Final concentration of the acid | PCA | | | TCA | | | HNO₃ | | |
|---|---|---|---|---|---|---|---|---|---|
| | Percent detection of the endotoxin | | Amidase activity (%) (*) | Percent detection of the endotoxin | | Amidase activity (%) (*) | Percent detection of the endotoxin | | Amidase activity (%) (*) |
| | Plasma | Physiological saline (control) | | Plasma | Physiological saline (control) | | Plasma | Physiological saline (control) | |
| 0 (non-treated) | — | 100 | 100 | — | 100 | 100 | — | 100 | 100 |
| 0.5 | 100 | 100 | 5 | 100 | 100 | 9 | 100 | 100 | 12 |
| 1.0 | 100 | 100 | 0 | 100 | 100 | 2 | 100 | 100 | 5 |
| 1.25 | 100 | 100 | 0 | 100 | 100 | 0 | 100 | 100 | 4 |
| 2.0 | 100 | 98 | 0 | 100 | 100 | 0 | 100 | 93 | 0 |
| 2.5 | 75 | 70 | 0 | 100 | 100 | 0 | 82 | 77 | 0 |
| 5.0 | 65 | 60 | 0 | 85 | 80 | 0 | 74 | 70 | 0 |
| 10.0 | 40 | 35 | 0 | 63 | 60 | 0 | 54 | 50 | 0 |

(*) The hydrolytic activity of an endotoxin-independent enzyme in the acid-treated assay sample.

According to the method of this invention, a decrease in percent detection, owing presumably to the decomposition of the endotoxin itself in the plasma sample or the physiological saline, was seen with some kinds of the acid treating agents when the final concentration of the acid increased beyond a certain value. But by properly selecting the type of the acid and/or the treating conditions by preliminary experiments, the true amount of an endotoxin in the biological sample can be easily detected and determined with accuracy, high reliability and good reproducibility under conditions which make the effect of the amidase activity negligible.

The method of this invention will be further illustrated by the following clinical data.

EXAMPLE 4

Plasma samples (PRP) were taken from a normal healthy person and patients with endotoxemia, and treated with PCA in accordance with the method of this invention. The amount of an endotoxin in these acid-treated plasma samples was determined by using the peptide-type synthetic substrate described in section (3) given hereinabove.

Figure 1:
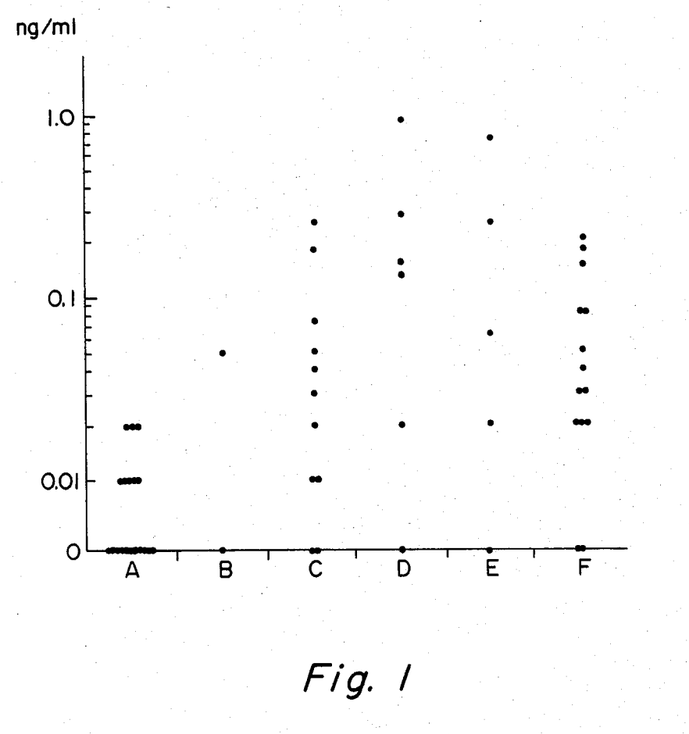

The results are shown in FIG. 1. It is seen from FIG. 1 that in the normal person (normal: A in the graph), the endotoxin was distributed between 0 and 0.02 ng/ml. In contrast, with the endotoxemia patients {B: hepatitis; C: liver cirrhosis; D: sepsis; E: malignant tumor; and F: leukemia}, the endotoxin was distributed over a broad range of from 0 to 1 ng/ml in different distribution patterns which can clearly distinguish from the endotoxin distribution pattern in the normal person. These results show that the method of this invention can determine the endotoxin with accuracy, high reliability and good reproducibility, and offers a useful technique for clinical diagnosis.

EXAMPLE 5

Endotoxin determination was carried out in the same way as in Example 4 using a plasma sample from T. K.

Each of the biological samples described above was subjected to the PCA treatment, TCA treatment and HNO₃ treatment to prepare acid-treated samples. The aforesaid endotoxin solution was added to each of the acid-treated samples so that its concentration was twice the amount of the endotoxin measured by the initial detecting test. Then, in the same way as in Example 4, the amount of the endotoxin in these samples was determined. The same test was conducted with regard to samples obtained by adding the aforesaid endotoxin solution before the acid treatment.

The results are shown in Tables 5 to 8.

It is seen from these results that irrespective of the types of the diseases and the biological samples, almost 100% of the endotoxin added was recovered, and the results were the same whether the endotoxin was added before or after the acid treatment of the biological samples. This means that when the assay samples are acid-treated in accordance with the method of this invention, the added endotoxin does not undergo deactivation, and the added endotoxin can be recovered almost in a theoretical amount without any adverse effects by the interaction between the added endotoxin and the assay sample or without any undesirable non-specific phenomena of LAL-Test inhibiting factors, amidase activity, etc. This further clarifies the excellent accuracy, high reliability and good reproducibility of the results of measurement obtained by the method of this invention.

TABLE 5

(Plasma; endotoxemia)

| Acid treatment | Amidase activity | Amount of the endotoxin detected (ng/ml) | Time of adding the endotoxin | Ratio of recovery (%) |
|---|---|---|---|---|
| PCA | 0 | 0.73 | Before acid-treatment | 108 |
| | | | After acid-treatment | 102 |
| TCA | 0 | 0.76 | Before acid-treatment | 105 |
| | | | After acid-treatment | 100 |
| HNO₃ | 0 | 0.75 | Before acid-treatment | 100 |

TABLE 5-continued (Plasma; endotoxemia)

| Acid treatment | Amidase activity | Amount of the endotoxin detected (ng/ml) | Time of adding the endotoxin | Ratio of recovery (%) |
|---|---|---|---|---|
| | | | After acid-treatment | 98 |

TABLE 6

(Serum, liver cirrhosis)

| Acid treatment | Amidase activity | Amount of the endotoxin detected (ng/ml) | Time of adding the endotoxin | Ratio of recovery (%) |
|---|---|---|---|---|
| PCA | 0 | 0.15 | Before acid-treatment | 110 |
| | | | After acid-treatment | 109 |
| TCA | 0 | 0.14 | Before acid-treatment | 106 |
| | | | After acid-treatment | 108 |
| HNO$_3$ | 0 | 0.15 | Before acid-treatment | 111 |
| | | | After acid-treatment | 100 |

TABLE 7

(Urine, urinary tract infection)

| Acid treatment | Amidase activity | Amount of the endotoxin detected (ng/ml) | Time of adding the endotoxin | Ratio of recovery (%) |
|---|---|---|---|---|
| PCA | 0 | 1.0 | Before acid-treatment | 104 |
| | | | After acid-treatment | 101 |
| TCA | 0 | 1.2 | Before acid-treatment | 103 |
| | | | After acid-treatment | 109 |
| HNO$_3$ | 0 | 1.1 | Before acid-treatment | 110 |
| | | | After acid-treatment | 108 |

TABLE 8

(Ascites, malignant tumor of the pancreas)

| Acid treatment | Amidase activity | Amount of the endotoxin detected (ng/ml) | Time of adding the endotoxin | Ratio of recovery (%) |
|---|---|---|---|---|
| PCA | 0 | 10 | Before acid-treatment | 102 |
| | | | After acid-treatment | 100 |
| TCA | 0 | 10 | Before acid-treatment | 97 |
| | | | After acid-treatment | 100 |
| HNO$_3$ | 0 | 9 | Before acid-treatment | 100 |
| | | | After acid-treatment | 110 |

The following Example shows embodiments of the kit of this invention.

EXAMPLE 6

A kit was prepared from a combination of the following materials.

| (1) | |
|---|---|
| 0.32M Perchloric acid | 5 ml per vial |
| 0.18N Sodium hydroxide | 2 ml per vial |
| 0.2M Tris-HCl buffer, pH 8.0 | 3 ml per vial |
| Lysate + substrate | 2.2 ml per vial |
| Sterilized distilled water | 10 ml per vial |
| Endotoxin | 20 ng per vial |
| 0.48N Hydrochloric acid | 15 ml per vial |
| Sodium nitrite | 4.8 mg per vial |
| Ammonium sulfamate | 36 mg per vial |
| N—(1-Naphthyl)ethylenediamine dihydrochloride | 8.4 mg per vial |

| (2) | |
|---|---|
| 0.32M Perchloric acid | 5 ml per ampoule |
| 0.18N Sodium hydroxide | 2 ml per ampoule |
| 0.2M Tris-HCl buffer, pH 8.0 | 3 ml per ampoule |
| Lysate + substrate | 2.2 ml per ampoule |
| Endotoxin | 20 ng per ampoule |

| (3) | |
|---|---|
| 0.32M Perchloric acid | 25 ml per vial |
| 0.18N Sodium hydroxide | 10 ml per vial |
| 0.2M Tris-HCl buffer, pH 8.0 | 15 ml per vial |
| Lysate + substrate | 11 ml per vial |
| Endotoxin | 1 µg per vial |
| 0.48N Hydrochloric acid | 75 ml per vial |
| Sodium nitrite | 24 mg per vial |
| Ammonium sulfamate | 180 mg per vial |
| N—(1-Naphthyl)ethylenediamine dihydrochloride | 42 mg per vial |

What we claim is:

1. In a method for qualitatively, semi-quantitatively or quantitatively determining a bacterial endotoxin in an assay sample by a gellation method or synthetic substrate method using an amoebocyte lysate component of horseshoe crab in the presence or absence of a substrate for endotoxin determination, the improvement wherein the determination by the gellation method or synthetic substrate method is effected by using an assay sample in the liquid state obtained by treating said assay sample with an endotoxin-free acid having a pKa$^{25°\,C.}$ value of not more than 3 at a pH of not more than 3, whereby the assay sample is freed from the hydrolytic activity of an endotoxin-independent enzyme, which is an inhibiting factor in measuring the true amount of the bacterial endotoxin in the assay sample.

2. The method of claim 1 wherein the pH of the assay sample in the liquid state is adjusted to 6–9 before the determination.

3. The method of claim 1 wherein the acid having a pKa$^{25°\,C.}$ value of not more than 3 is selected from the group consisting of mineral acids, halogenic acids, perhalogenic acids and haloacetic acids.

4. A kit for the determination of a bacterial endotoxin in an assay sample using an amoebocyte lysate component of horseshoe crab in the presence or absence of a substrate for endotoxin determination, said kit consisting essentially of a receptacle containing (a) an endotoxin-free acid having a pKa$^{25°\,C.}$ value of not more than 3 for treating the assay sample and a receptacle containing (b) an amoebocyte lysate component of horseshoe crab in amounts sufficient for bacterial endotoxin determination in the acid-treated assay sample.

5. The kit of claim 4 wherein the receptacle containing the component (b) also contains an endotoxin-free substrate (c) for bacterial endotoxin determination in the acid-treated assay sample.

6. The kit of claim 4 which further comprises a receptacle containing (c) an endotoxin-free substrate for bacterial endotoxin determination in the acid-treated assay sample.

7. The kit of claim 4 which further comprises a receptacle containing (d) an endotoxin-free alkali for neutralizing the acid-treated assay sample.

8. The kit of claim 5 or 6 which further comprises a receptacle containing (d) an endotoxin-free alkali for neutralizing the acid-treated assay sample.

9. The kit of claim 4 which further comprises a receptacle containing (e) an endotoxin-free diluent or its frozen product for diluting the assay sample.

10. The kit of claim 4 which further comprises a receptacle containing (f) an endotoxin-free buffer.

11. A method of pre-treating an assay sample for the determination of bacterial endotoxin in the assay sample using an amoebocyte lysate component of horseshoe crab in the presence or absence of a substrate for endotoxin determination, said method comprising treating said assay sample with an endotoxin-free acid having a $pKa^{25°C}$ value of not more than 3 at a pH of not more than 3, whereby the assay sample is freed from the hydrolytic activity of an endotoxin-independent enzyme, which is an inhibiting factor in measuring the true amount of the bacterial endotoxin in the assay sample.

12. The method of claim 11 wherein the acid having a $pKa^{25°C}$ value of not more than 3 is selected from the group consisting of mineral acids, halogenic acids, perhalogenic acids and haloacetic acids.

13. The method of claim 11 which further comprises adjusting the pH of the acid treated assay sample to the range from 6 to 9.

14. The method of claim 11 wherein the assay sample is a biological fluid containing proteins or cell granules susceptible to endotoxin absorption selected from the group consisting of plasma, serum, blood fractions, ascites, articular fluid and urine.

15. The method of claim 11 wherein the assay sample is a biological preparation selected from the group consisting of bacterial vaccines, viral vaccines, and blood preparations.

* * * * *